US012678162B2

(12) United States Patent
Purohit et al.

(10) Patent No.: US 12,678,162 B2
(45) Date of Patent: Jul. 14, 2026

(54) SYSTEMS, DEVICES, AND RELATED METHODS FOR FASTENING TISSUE

(71) Applicant: BOSTON SCIENTIFIC MEDICAL DEVICE LIMITED, Galway (IE)

(72) Inventors: Hitendra Purohit, Vadodara (IN); Yogesh Kishor Vikharankar, Pune (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 0 days.

(21) Appl. No.: 18/931,529

(22) Filed: Oct. 30, 2024

(65) Prior Publication Data

US 2025/0134522 A1     May 1, 2025

Related U.S. Application Data

(60) Provisional application No. 63/594,775, filed on Oct. 31, 2023.

(51) Int. Cl.
    *A61B 17/064*       (2006.01)
    *A61B 17/072*       (2006.01)
(52) U.S. Cl.
    CPC ................... *A61B 17/07207* (2013.01); *A61B 2017/07257* (2013.01); *A61B 2017/07271* (2013.01); *A61B 2017/07278* (2013.01)
(58) Field of Classification Search
    CPC .... A61B 17/07207; A61B 2017/07257; A61B 2017/07271; A61B 2017/07278
    See application file for complete search history.

(56) References Cited

U.S. PATENT DOCUMENTS

| | | | |
|---|---|---|---|
| 5,452,837 A | * | 9/1995 | Williamson, IV .......................... A61B 17/07207 227/176.1 |
| 5,669,875 A | | 9/1997 | van Eerdenburg |
| 7,500,979 B2 | | 3/2009 | Hueil et al. |
| 7,857,185 B2 | | 12/2010 | Swayze et al. |
| 8,127,976 B2 | | 3/2012 | Scirica et al. |
| 8,322,455 B2 | | 12/2012 | Shelton, IV et al. |
| 8,998,935 B2 | | 4/2015 | Hart |

(Continued)

FOREIGN PATENT DOCUMENTS

| | | | |
|---|---|---|---|
| WO | 2003094747 A1 | 11/2003 | |
| WO | WO-2021080976 A1 * | 4/2021 | ....... A61B 17/07207 |

OTHER PUBLICATIONS

International Search Report and Written Opinion in Application No. PCT/IB2024/060710, dated Jan. 29, 2025 (14 pages).

*Primary Examiner* — Eyamindae C Jallow
(74) *Attorney, Agent, or Firm* — Bookoff McAndrews PLLC

(57) ABSTRACT

Disclosed is a medical device including an end effector having an upper arm including: a first plurality of teeth and a second plurality of teeth; a lower arm including a third plurality of teeth, a fourth plurality of teeth, and an anvil. The third plurality of teeth may be on a first lateral side of the anvil and the fourth plurality of teeth may be on a second lateral side of the anvil. A cartridge may be positioned in a cavity of the upper arm, such that the first plurality of teeth are on a first lateral side of the cartridge and the second plurality of teeth are on the second lateral side of the cartridge. Further, a shaft may be coupled to the end effector; and an operation portion may be coupled to the shaft.

20 Claims, 11 Drawing Sheets

(56) References Cited

U.S. PATENT DOCUMENTS

| | | | |
|---|---|---|---|
| 10,548,599 B2 | 2/2020 | Marczyk et al. | |
| 11,147,551 B2 | 10/2021 | Shelton, IV | |
| 11,147,553 B2 | 10/2021 | Shelton, IV | |
| 11,517,305 B2 | 12/2022 | Valentine, Jr. et al. | |
| 11,642,126 B2 | 5/2023 | Beardsley | |
| 2006/0047303 A1* | 3/2006 | Ortiz ................ | A61B 17/07207 606/205 |
| 2013/0240599 A1* | 9/2013 | Scirica ................... | A61B 90/92 227/176.1 |
| 2014/0021240 A1 | 1/2014 | Miyamoto | |
| 2014/0076955 A1* | 3/2014 | Lorenz ............ | A61B 17/07207 227/176.1 |
| 2019/0201040 A1* | 7/2019 | Messerly ......... | A61B 17/07207 |
| 2020/0337695 A1 | 10/2020 | Xu | |
| 2021/0177410 A1 | 6/2021 | Williams | |
| 2021/0275174 A1* | 9/2021 | Vadali .............. | A61B 17/07292 |
| 2023/0076091 A1* | 3/2023 | Zhou ................ | A61B 17/07207 |
| 2024/0350143 A1* | 10/2024 | Yee .................. | A61B 17/07207 |

* cited by examiner

SYSTEMS, DEVICES, AND RELATED METHODS FOR FASTENING TISSUE

CROSS-REFERENCE TO RELATED APPLICATIONS

This application claims the benefit of priority of U.S. Provisional Patent Application No. 63/594,775 filed Oct. 31, 2023, the entirety of which is incorporated herein by reference.

TECHNICAL FIELD

This disclosure relates generally to tissue closure. More particularly, at least some embodiments of this disclosure relate to a stapling device or system, for example an endoscopic stapler, and related methods of using the stapling device or system.

BACKGROUND

An endoscopic procedure typically involves indirect observation of a surgical field through an endoscope or similar device inserted through an incision or a natural anatomical opening. The endoscope generally takes the form of a long, flexible tube, including a light conductor along with one or more channels for inserting medical devices. Endoscopes provide platforms for employing numerous tools as end-effectors, such as devices to grasp and staple tissue inside the body. For example, accessory devices such as graspers may be used to grip tissue, and staplers may be used to secure tissue.

SUMMARY

Aspects of this disclosure relate to, among other things, systems, devices, and methods for fastening tissue. Each of the aspects disclosed herein may include one or more of the features described in connection with any of the other disclosed aspects.

In an example, a medical device may include an end effector having an upper arm including: a first plurality of teeth; and a second plurality of teeth; a lower arm including: a third plurality of teeth; a fourth plurality of teeth; and an anvil. The third plurality of teeth may be on a first lateral side of the anvil and the fourth plurality of teeth may be on a second lateral side of the anvil. The second lateral side of the anvil may be opposite the first lateral side of the anvil; and a cartridge may be positioned in a cavity of the upper arm, such that the first plurality of teeth are on a first lateral side of the cartridge and the second plurality of teeth are on the second lateral side of the cartridge, such that the second lateral side of the cartridge is opposite the first lateral side of the cartridge. Further, a shaft may be coupled to the end effector; and an operation portion may be coupled to the shaft.

Any of the aspects disclosed herein may include any of the following features, alone or in any combination. A cable may be coupled to the upper arm, the cable configured to rotate the upper arm; and a tube coupled to a sled received within the cartridge, the sled configured to deliver staples; wherein at least a portion of the cable is disposed within the tube. The cable may be coupled to a trigger of the operation portion. The tube may be coupled to a slider of the operation portion. A distal portion of the upper arm may include a protrusion; and a distal portion of the lower arm includes a recess configured to mate with the protrusion. Each of the third plurality of teeth and the fourth plurality of teeth of the lower arm may include a plurality of ridges and a plurality of recesses, such that the plurality of recesses are recessed with respect to a surface of the anvil. The surface of the anvil may be planar. Upper surfaces of the third plurality of teeth and upper surfaces of the fourth plurality of teeth may be approximately level with the surface of the anvil. Each of the first plurality of teeth and the second plurality of teeth may include a plurality of ridges and a plurality of recesses. Lower surfaces of the plurality of ridges of the first plurality of teeth and lower surfaces of the plurality of ridges of the second plurality of teeth may be below the surface of the anvil when the end effector is in a closed configuration. The upper surfaces of the plurality of recesses of the first plurality of teeth and the plurality of recesses of the second plurality of teeth of the upper arm may be approximately level with the anvil in the closed configuration. The third plurality of teeth and the fourth plurality of teeth may be arranged approximately linearly. The lower arm further may include a first distal tooth distal of the first plurality of teeth and a second distal tooth distal of the second plurality of teeth. The first distal tooth and the second distal tooth may be disposed on a curved surface between a lateral side surface of the lower arm and a distal surface of the lower arm. The first plurality of teeth and the second plurality of teeth may extend downward from a surface of the upper arm that defines the cavity. The cavity may have an open proximal end for slidably receiving the cartridge or an open distal end for slidably receiving the cartridge. The cavity may have a first stepped portion, and the cartridge may have a second stepped portion configured to mate with the first stepped portion.

In another aspect, a medical device may include: an end effector having: an upper arm including a first plurality of teeth; a lower arm including a second plurality of teeth and an anvil; and a cartridge positioned in a cavity of the upper arm; a shaft coupled to the end effector, the shaft including: a cable coupled to the upper arm, the cable configured to rotate the upper arm; and a tube coupled to a sled received within the cartridge, the sled configured to deliver staples. The cable may be at least partially disposed within the tube, and include an operation portion coupled to the shaft.

Any of the aspects disclosed herein may include any of the following features, alone or in any combination. The cavity may have an open proximal end for slidably receiving the cartridge, or wherein the cavity has an open distal end for slidably receiving the cartridge.

In yet another aspect, a medical device may include: an end effector having: an upper arm including a first plurality of teeth; a lower arm including a second plurality of teeth and an anvil. The second plurality of teeth may include a plurality of ridges and a plurality of recesses. The plurality of recesses may be recessed with respect to a surface of the anvil. The end effector may also have: a cartridge positioned in a cavity of the upper arm; a shaft coupled to the end effector; and an operation portion coupled to the shaft.

Any of the aspects disclosed herein may include any of the following features, alone or in any combination. The surface of the anvil may be planar, and the upper surfaces of the second plurality of teeth may be approximately level with the surface of the anvil. The first plurality of teeth may include: a plurality of ridges and a plurality of recesses The lower surfaces of the plurality of ridges of the first plurality of teeth may be below the surface of the anvil when the end effector is in a closed configuration.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

DETAILED DESCRIPTION

Figure 1:
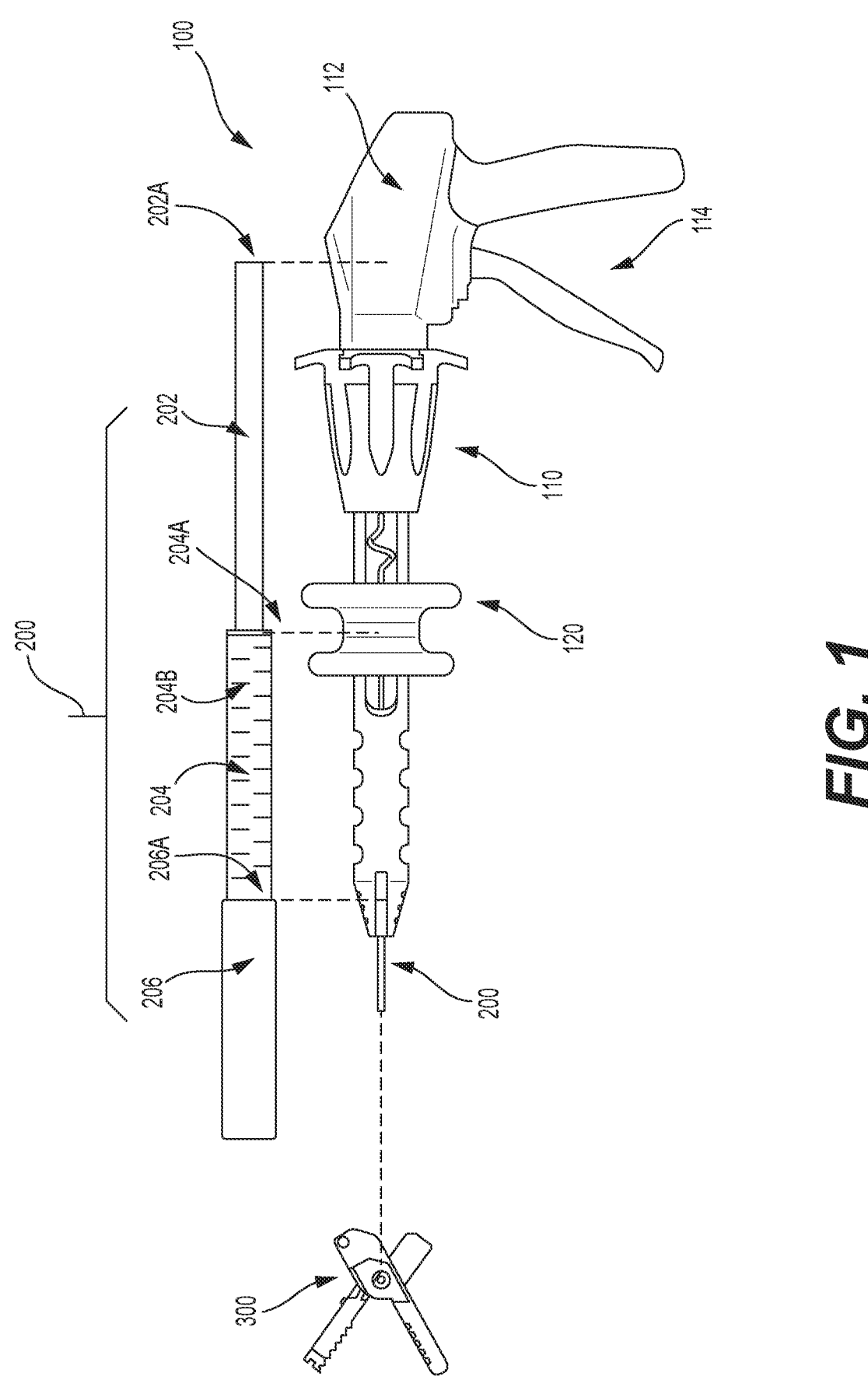
FIG. 1 depicts an exemplary medical device, according to one or more embodiments.

During surgical procedures, precision end-effectors are important to ensure safe, effective, quick, and successful outcomes. Additionally, time and effort required to exchange accessory devices during surgery may lengthen and complicate a procedure. A single accessory device having multiple functionalities may reduce the use of multiple devices thereby reducing the time and complexity of the procedure.

This disclosure is drawn to systems, devices, and methods for grasping and stapling tissue, among other aspects. Reference will now be made in detail to aspects of this disclosure, examples of which are illustrated in the accompanying drawings.

Wherever possible, the same or similar reference numbers will be used throughout the drawings to refer to the same or like parts. The term "distal" refers to a portion further away from a user when introducing a device into a subject. By contrast, the term "proximal" refers to a portion closer to the user when placing the device into the subject. Directions, such as "up," "down," "top," "bottom," "left," "right," and the like refer to an orientation as shown in the figures, even if a device is capable of being reoriented.

Both the foregoing general description and the following detailed description are exemplary and explanatory only and are not restrictive of the features, as claimed. As used herein, the terms "comprises," "comprising," "has," "having," "includes," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−10% of the stated value unless otherwise stated.

The disclosure provides a medical device including a tissue grasper having two arms forming a jaw-like structure. The tissue grasper may be an end effector for holding and manipulating tissue and other target objects. Manipulating may include, but is not limited to, clamping and stapling. The arms of the end effector may be rotatably connected to one another to permit the arms to move between an open and closed configuration. A proximal portion of one or both arms may be operably connected to one or more control members. The control member(s) may extend through an elongated member (e.g., a shaft) extending between the end effector at a distal end of the device to an end effector actuator or other type of controller present at its proximal end (e.g., an actuator of a handle). Activating the actuator actuates the end effector to effectuate opening and closing of the arms, among other aspects. The two arms may be differentiated as an "upper" and "lower" arm. The handle may also include another actuator to deploy staples from the end effector into tissue. Various exemplary configurations of end effector actuation, structure, and functions are described in the embodiments of the disclosure. It will be appreciated that any of the aspects disclosed herein may be utilized alone or together, in any combination or subcombination.

Aspects disclosed herein may include a handle, a flexible shaft, and an end effector (e.g., stapler head). The end effector may include a sled that includes a slider (e.g., a ramp assembly). The sled may be coupled to one or more wires or wire segments, such that the sled may be actuated proximally and/or distally. The handle or other operation portion may include actuators for, among other features, opening/closing the end effector, actuating the sled, articulating the shaft, and/or rotating the end effector about a longitudinal axis of the device.

FIGS. 1-6B illustrate aspects of an exemplary medical device 100 that may be used to staple tissue of a subject. In some embodiments, medical device 100 may be a surgical stapling apparatus configured to engage body tissue, apply one or more surgical fasteners (e.g., staplers) thereto during minimally invasive surgical procedures, such as endoscopic procedures. Medical device 100 may be used to apply other fasteners (e.g., clips, elastic bands, sutures, etc.), but will be primarily discussed in the context of applying staples. The fasteners may be used to fasten tissue (e.g., staple, fix, attach, fasten, or otherwise join two or more portions of tissue together).

As shown particularly in FIG. 1, medical device 100 may include a handle 110 (an operation portion), a shaft 200, and an end effector 300. FIG. 1 depicts details of shaft 200 above the depiction of device 100 in order to show relative positions of components of shaft 200 relative to handle 110. As described below, handle 110 may include one or more actuators for actuating aspects of shaft 200 and/or end effector 300. Handle 110 may include a body 112 and various actuators for controlling aspects of shaft 200 and/or end effector 300. For example, handle 110 may include a trigger 114, which may be a first actuator that is movable relative to body 112. Handle 110 may also include a slider 120 (e.g., a spool), which may be a second actuator that is movable relative to body 112. Handle 110 may further include other actuators, such as tabs, knobs, levers, or other actuators. Although ordinal numbers, such as "first," "second," etc. are used to describe actuators of handle 110 herein, it will be appreciated that such terms are merely for reference and that any ordinal number may be applied to any of the actuators. Furthermore, the types of actuators described herein are merely exemplary, and any alternative type of actuator may be used. The figures depicting aspects of handle 110 may omit certain features in order to depict details related to a particular actuator or other aspect of handle 110.

Trigger 114 may be coupled to a cable 202, or other actuation/control member. For example, trigger 114 may be coupled to cable 202 via a linkage. The linkage may be monolithically formed with cable 202 (formed of a single, integral piece) or may be a separate piece/member from cable 202 that is coupled to cable 202. Trigger 114 may alternatively be directly connected to cable 202. Although the term "cable" is used herein to describe various structures, it will be appreciated that these structures may be other types of control/actuation mechanisms (e.g., wires, sliders, linkages, bars, etc.). Furthermore, any of the cables disclosed herein may be a segment that may be combined with other control members of the same or different types. Cable 202 may be formed from metal or other suitable strong and flexible material. Although not shown. A user may squeeze trigger 114 toward body 112 (e.g., proximally), thereby moving the linkage and cable 202 proximally (applying tension to cable 202). As discussed below, proximal movement of cable 202 may actuate end effector 300.

Slider 120 may be movable in a direction that is approximately coaxial with or parallel to a central longitudinal axis of handle 110. Slider 120 may be coupled to a tube 204 (e.g., an intermediate tube), discussed in more detail below. Although the term "tube" is used herein, it will be appreciated that the term encompasses structures such as coils, rings, multilumen extrusions, hypotubes, etc. Tube 204 may be formed from metal or other suitable strong and flexible material, such as a polymer. Tube 204 may include slits (e.g., laser cuts) 204B to increase the flexibility of tube 204.

Shaft 200 may be any suitable endoscopic member configured to bend and/or articulate so as to traverse tortuous anatomy in a body. Shaft 200 may include an outer tube 206 formed from one or more biocompatible materials, such as, e.g., HDPE, silicone, polyurethane, ETFE, SIBS, PIB-PUR, or any other suitable medical grade polymers, and may be flexible and configured to extend through tortuous anatomy. Shaft 200 may extend any length suitable for endoscopic or laparoscopic procedures, and may be configured to be positioned within a working channel of an endoscope. Alternatively, shaft 200 may be positioned in the body without an endoscope. Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, laproscopes, catheters, diagnostic or therapeutic tools or devices, or other types of medical devices.

Figure 2:
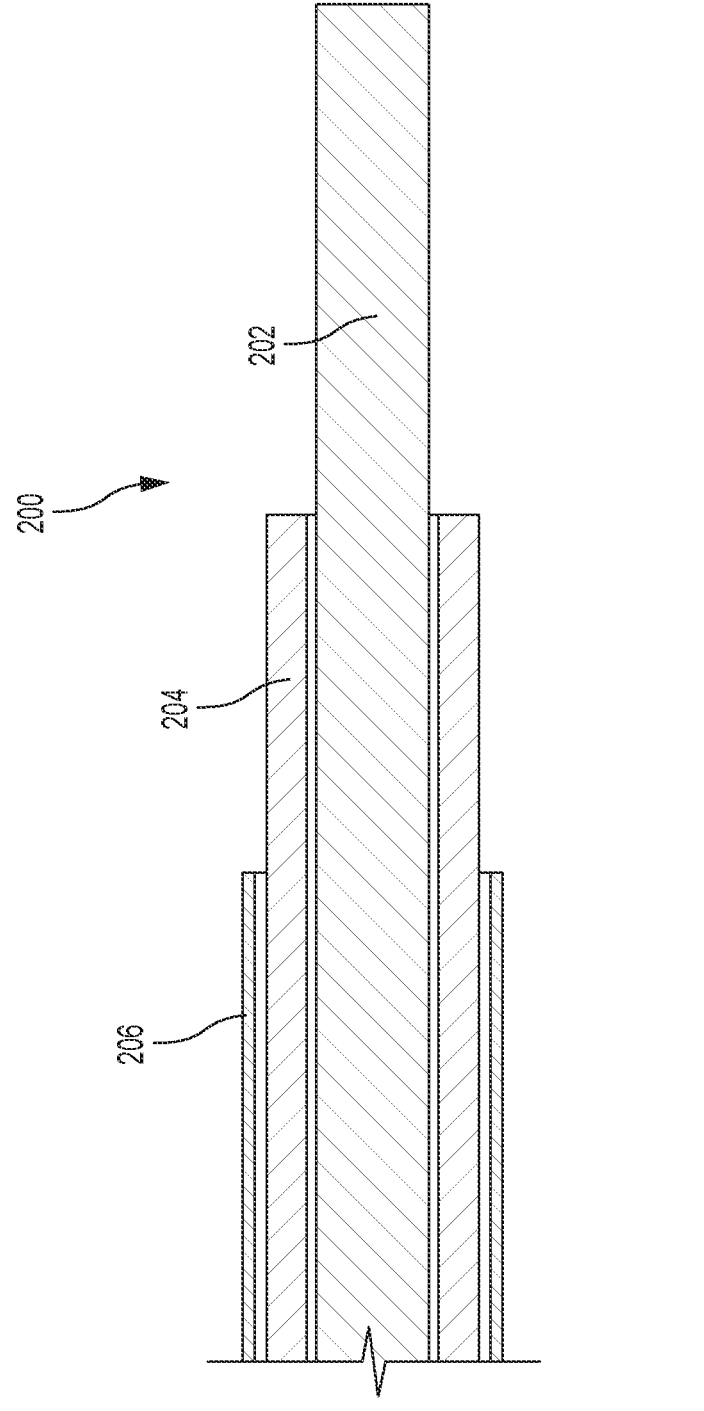
FIG. 2 depicts a cross-section of a catheter of the exemplary medical device, according to one or more embodiments.

As shown in FIGS. 1 and 2, the interior cable 202, intermediate tube 204, and outer tube 206 may be telescopically formed and extend varying distances in the proximal direction. Interior cable 202 extends furthest proximally of the three, extending to trigger 114 within the body 112 of handle 110, indicated by position 202A in FIG. 1, connecting with trigger 114 so that it may be actuated by the trigger 114 (e.g., via a linkage, as discussed above). Intermediate tube 204 extends proximally to and is actuated by the slider 120. A location where intermediate tube 204 is coupled to slider 120 is indicated by position 204A in FIG. 1. Outer tube 206 includes an interior channel (e.g., a lumen) for actuator elements such as cable 202 and intermediate tube 204, among other functions. As shown in FIG. 2, interior cable 202 is positioned within and surrounded by intermediate tube 204, and intermediate tube 204 is respectively positioned within and surrounded by outer tube 206, with a small gap between each respective element, such that cable 202 is movable longitudinally relative to tube 204. Similarly, the tube 204 is positioned within and surrounded by outer tube 206. Outer tube 206 may terminate at a distal portion of the handle at position 206A. The shaft 200 extends from handle 110 to end effector 300, where the actuator cables (cable 202 and tube 204) actuate elements in the end effector 300.

Figure 3A:
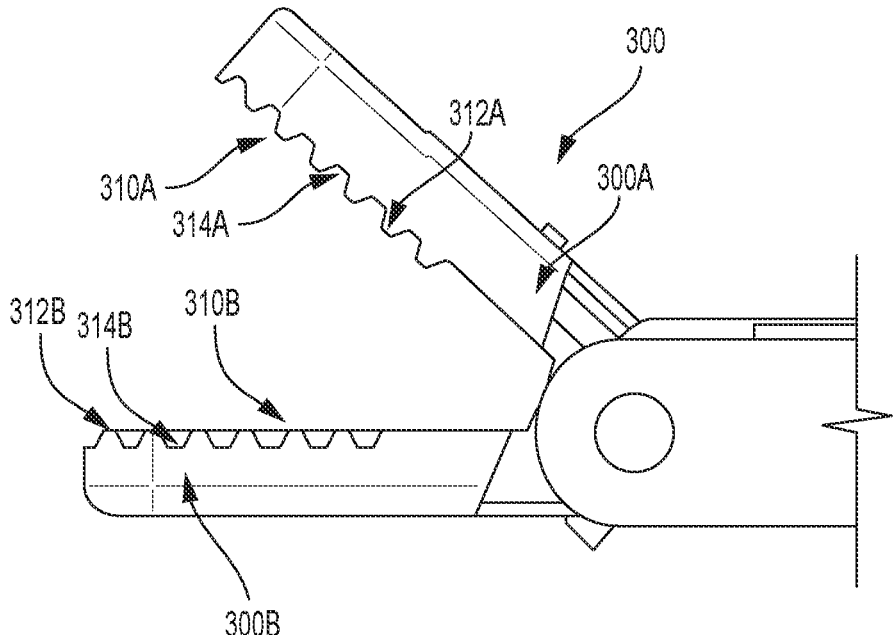
FIGS. 3A and 3B depict a distal portion of the medical device in a first configuration in a side view and a perspective view, respectively, according to one or more embodiments.

FIG. 3A depicts an end effector 300 in a first configuration in a side view, the first configuration being a configuration in which the end effector is open, whereby an upper arm (upper jaw) 300A is separated from a lower arm (lower jaw) 300B. In the example shown in FIGS. 3A and 3B, end effector 300 is configured for grasping and stapling. Upper arm 300A and/or lower arm 300B may be coupled to cable 202. Upper arm 300A and/or lower arm 300B may be actuated to rotate by manipulation of the trigger 114, which may translate cable 202 (move cable 202 proximally or distally). For example, proximal movement of cable 202 may cause upper arm 300A and/or lower arm 300B to rotate to an open position, and distal movement of cable 202 may cause upper arm 300A and/or lower arm 300B to rotate to a closed position. In some examples, cable 202 may be coupled only to upper arm 300A to cause rotation of upper arm 300A while lower arm 300B is stationary. Alternatively, both upper arm 300A and lower arm 300B may be coupled to cable 202 (e.g., via a linkage) and thereby rotated. Rotation of upper arm 300A and/or 300B may be effected by any mechanism known in the art (e.g., linkages and the like)

Figure 3B:
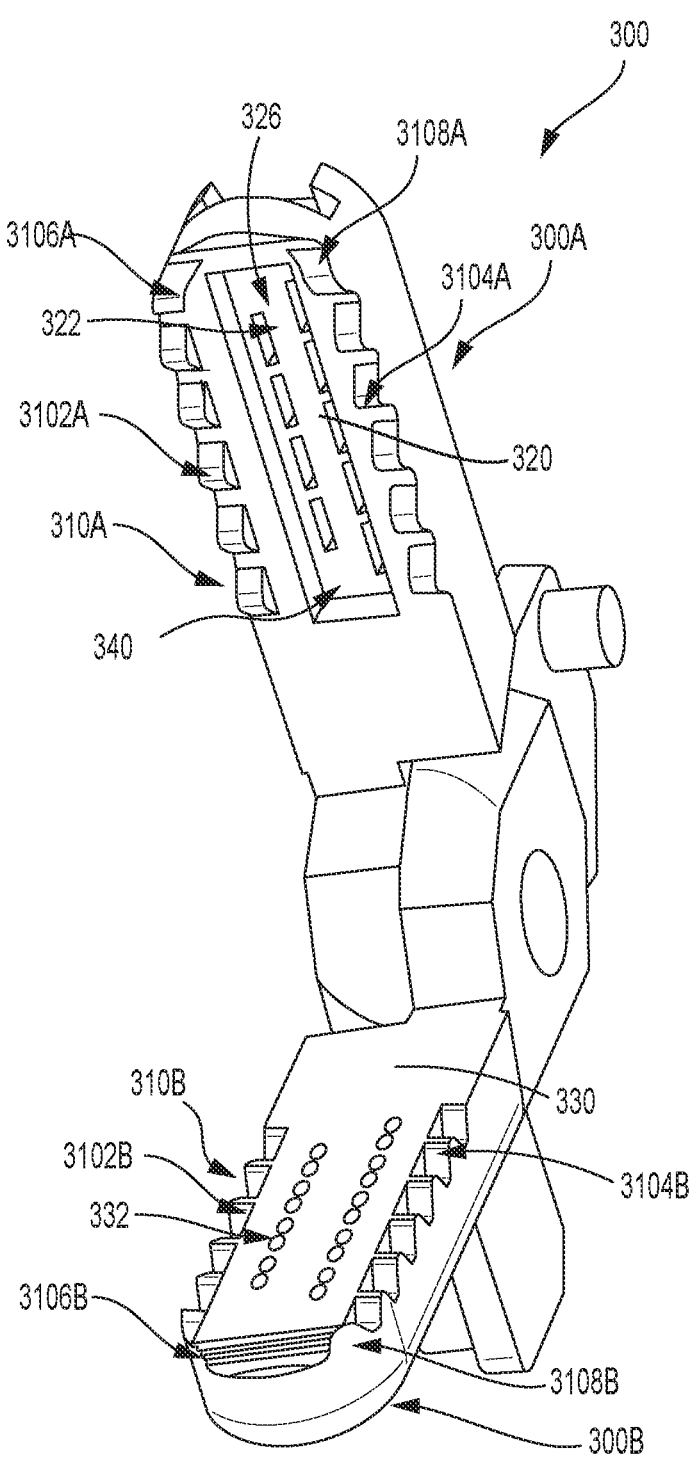

Upper arm 300A includes one or more upper teeth 310A, arranged on lateral sides of the upper arm 300A. In some embodiments, the upper teeth 310A may be arranged on a perimeter of upper arm 300A on the lateral sides of upper arm 300A. The teeth 310A comprise a series of ridges 312A and grooves 314A of suitable dimension. For example, in some embodiments, the teeth 310A may have a height in the range of 0.0040 to 0.0100 inches, and a width as measured from the top of one of the ridges 312A to an adjacent ridge 312A of between 0.0030 to 0.0036 inches. As shown in FIGS. 3A and 3B, ridges of teeth 310A may have a rounded "V" shape or a "U" shape with tapering sides. Alternatively, in other embodiments, the ridges may be rectangular, semicircular, or a combination of shapes. Teeth 310A may include a first set of teeth 3102A (having corresponding ridges and grooves) on a first side of a central longitudinal axis of upper arm 300A and a second set of teeth 3104A on a second, opposite side of the central longitudinal axis of upper arm 300A. In some aspects, first set of teeth 3102A and second set of teeth 3104A may be symmetrical to one another about the central longitudinal axis of upper arm 300A. First set of teeth 3102A and second set of teeth 3104A may extend approximately linearly, parallel to the central longitudinal axis of upper arm 300A. In some aspects, a distalmost ridge 3106A, 3108A of each of first set of teeth 3102A and second set of teeth 3104A, respectively, may be on a curved surface between a respective lateral side surface of upper arm 300A and a distal end surface end of upper arm 300A. Although distalmost ridge 3106A, 3108A may be considered as part of first set of teeth 3102A or second set of teeth 3104A, distalmost ridge 3106A, 3108A may alternatively be considered as separate from first set of teeth 3102A or second set of teeth 3104A. In some examples, each ridge of first set of teeth 3102A and second set of teeth 3104A may have a same height. Alternative, the ridges may have varying heights.

Lower arm 300B likewise comprises lower teeth 310B. In some embodiments, the lower teeth 310B may be arranged on a perimeter of lower arm 300B, including on lateral sides of lower arm 300B. The teeth 310B comprise a series of ridges 312B and grooves 314B of suitable dimension and are configured to correspond to and the teeth 310A such that in a closed configuration (see FIG. 4B), ridges 312B of lower teeth 310B are inserted into grooves 314A of upper teeth 310A, and ridges 312A of upper teeth 310A are inserted into grooves 314B of lower teeth 310B so that the teeth 310A, 310B intersect when the jaws of the upper arm 300A and lower arm 300B close. Ridges 312B and grooves 314B may have any of the features (e.g., shapes, etc.) of ridges 312A and grooves 314A, discussed above. Ridges 312B may lie parallel to one another on any axis (e.g., along a longitudinal axis).

Teeth 310B may include a first set of teeth 3102B (having corresponding ridges and grooves) on a first side of a central longitudinal axis of lower arm 300B and a second set of teeth 3104B on a second, opposite side of the central longitudinal axis of lower arm 300B. In some aspects, first set of teeth 3102B and second set of teeth 3104B may be symmetrical to one another about the central longitudinal axis of lower arm 300B. First set of teeth 3102B and second set of teeth 3104B may extend approximately linearly, parallel to the central longitudinal axis of lower arm 300B. In some aspects, a distalmost ridge 3106B, 3108B of each of first set of teeth 3102B and second set of teeth 3104B, respectively, may be on a distal end surface end of lower arm 300B or on a curved surface joining a lateral surface of lower arm 300B to a distal end surface of lower arm 300B. Although distalmost ridge 3106B, 3108B may be considered as part of first set of teeth 3102B or second set of teeth 3104B, distalmost ridge 3106B, 3108B may alternatively be considered as separate from first set of teeth 3102B or second set of teeth 3104B. In some examples, each ridge of first set of teeth 3102B and second set of teeth 3104B may have a same height. Alternative, the ridges may have varying heights.

As shown particularly in FIG. 6B, discussed below, upper arm 300A may include a protrusion 342 on a distal end 346 of upper arm 300A. Lower arm 300B may include a corresponding recess 344 on a distal end 348 of lower arm 300B. Protrusion 342 may be similar to a tooth and may function as a tooth. Protrusion 342 and recess 344 may extend along all or most of distal ends 346, 348, respectively. When end effector 300 is in a closed configuration, as shown in FIG. 6B, for example, protrusion 342 may be received within recess 344 such that a lower surface of protrusion 342 contacts or is near to a surface of recess 344.

As shown in FIG. 3B, upper arm 300A includes a cavity 340 for receiving a staple cartridge 320 arranged between first set of teeth 3102A and second set of teeth 3102B. Staple cartridge 320 may have staples 322 (FIGS. 5A, 5B, 6A) arranged therein. As shown in FIG. 3B, upper teeth 310A may extend downwardly (toward lower arm 300B) past a lower surface of staple cartridge 320. In some examples, upper surfaces of recesses between ridges of upper teeth 310A may be approximately level with a lower surface of staple cartridge 320.

Lower arm 300B includes a level surface (e.g., a planar surface) forming an anvil 330. Anvil 330 may include recesses 332 for receiving staples 322. Anvil 330 may be positioned between is surrounded on lateral sides by the lower teeth 310B, between first set of lower teeth 3102B and second set of lower teeth 3104B. In some examples, as shown particularly in FIG. 3B, an upper surface of the ridges of lower teeth 310B may be approximately level with a planar top surface of anvil 330. Lower arm 300B may be a single, monolithic piece with the lower teeth 310B and the anvil 330 formed of a single piece of material. Recesses between the ridges of lower teeth 310B may be formed in a surface of lower arm 300B that is to either lateral side of anvil 330.

Thus, teeth 310A, 310B may be formed on only a perimeter of upper arm 300A and lower arm 300B, respectively. Central portions of upper arm 300A and lower arm 300B, defining cavity 340 for receiving cartridge 320 and anvil 330, respectively, may lack teeth 310A, 310B. Similarly, protrusion 342 and recess 344 of distal ends 346, 348 may be on a distal portion of a perimeter of upper arm 300A, 310B, respectively. Cartridge 320/cavity 340 may terminate proximally of protrusion 342, and anvil 330 may terminate proximally of recess 344.

Figure 4A:
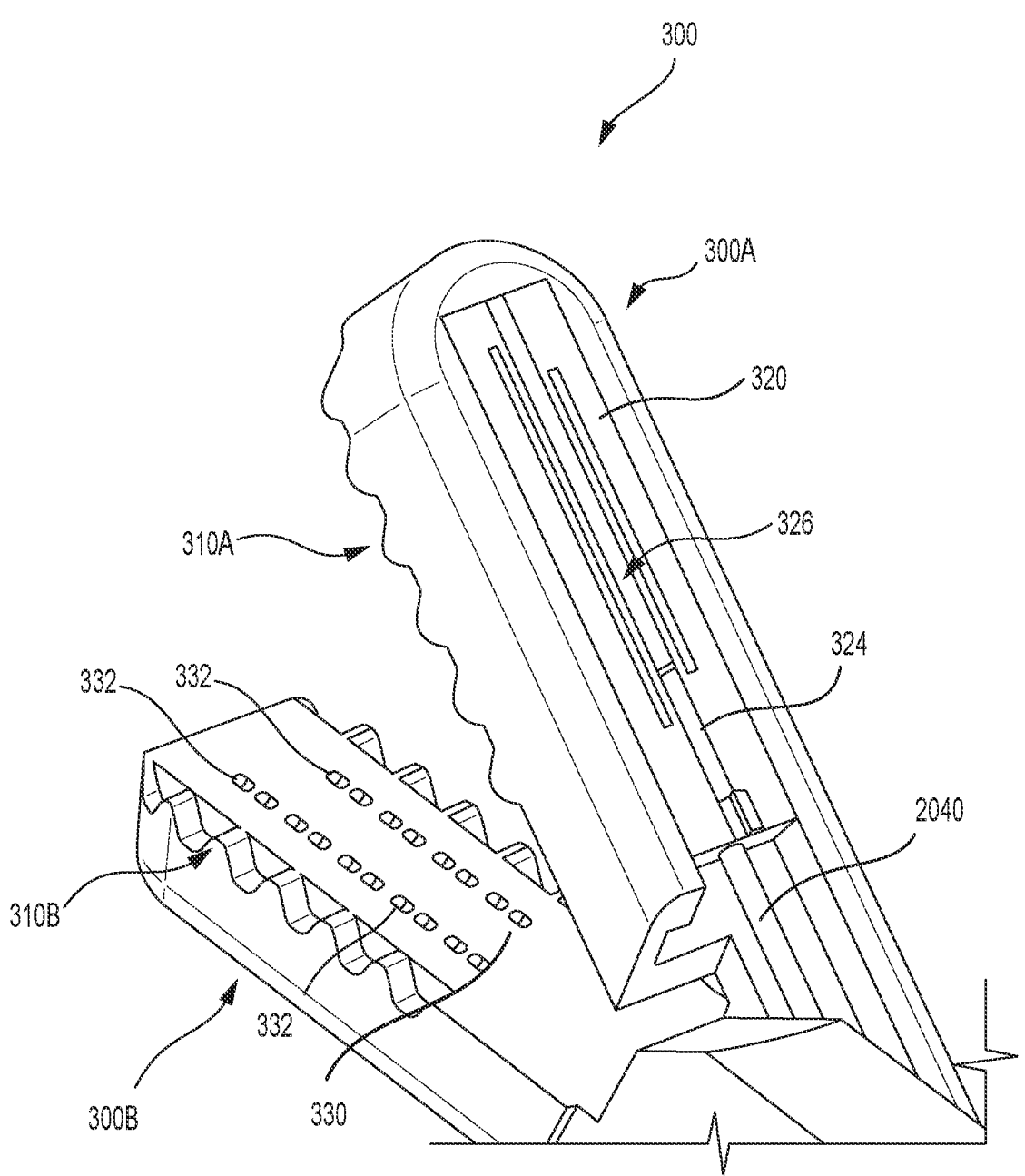
FIGS. 4A and 4B depict perspective views of the distal portion in a first configuration and a second configuration, respectively, according to one or more embodiments.
Figure 4B:
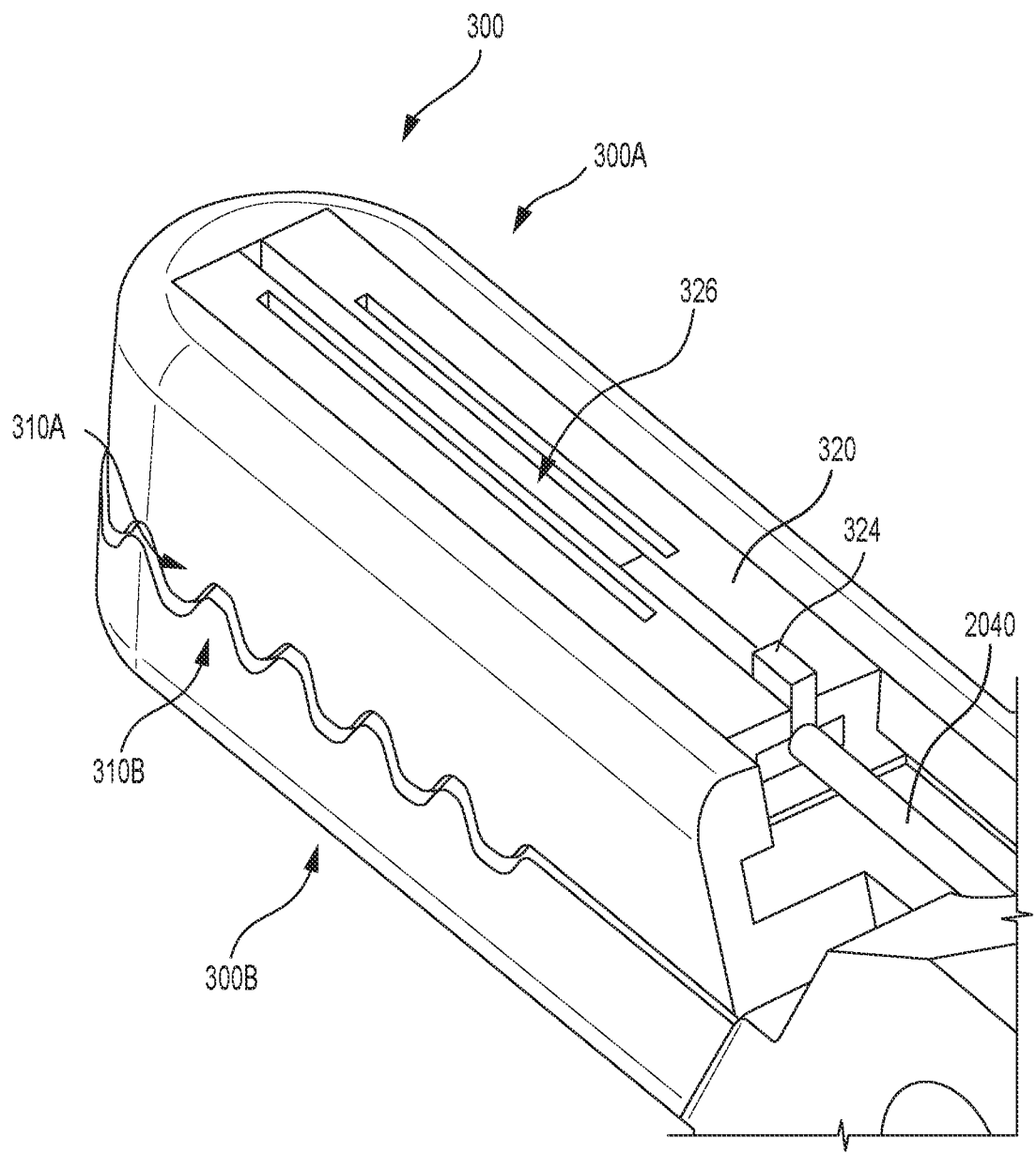

FIGS. 4A and 4B depict perspective views of the end effector 300 in the first, open configuration (FIG. 4A) and a second closed configuration (FIG. 4B), respectively, according to one or more embodiments. In the first configuration, upper arm 300A is rotated away from lower arm 300B, as in FIGS. 3A and 3B. In the second configuration, upper arm 300A is approximately parallel to lower arm 300B, and one or more portions of upper arm 300A and lower arm 300B (e.g., teeth 310A, 310B) may contact one another. Staple cartridge 320 is situated inside cavity 340 and rotates with upper arm 300A between the first and the second configurations.

Figure 5A:
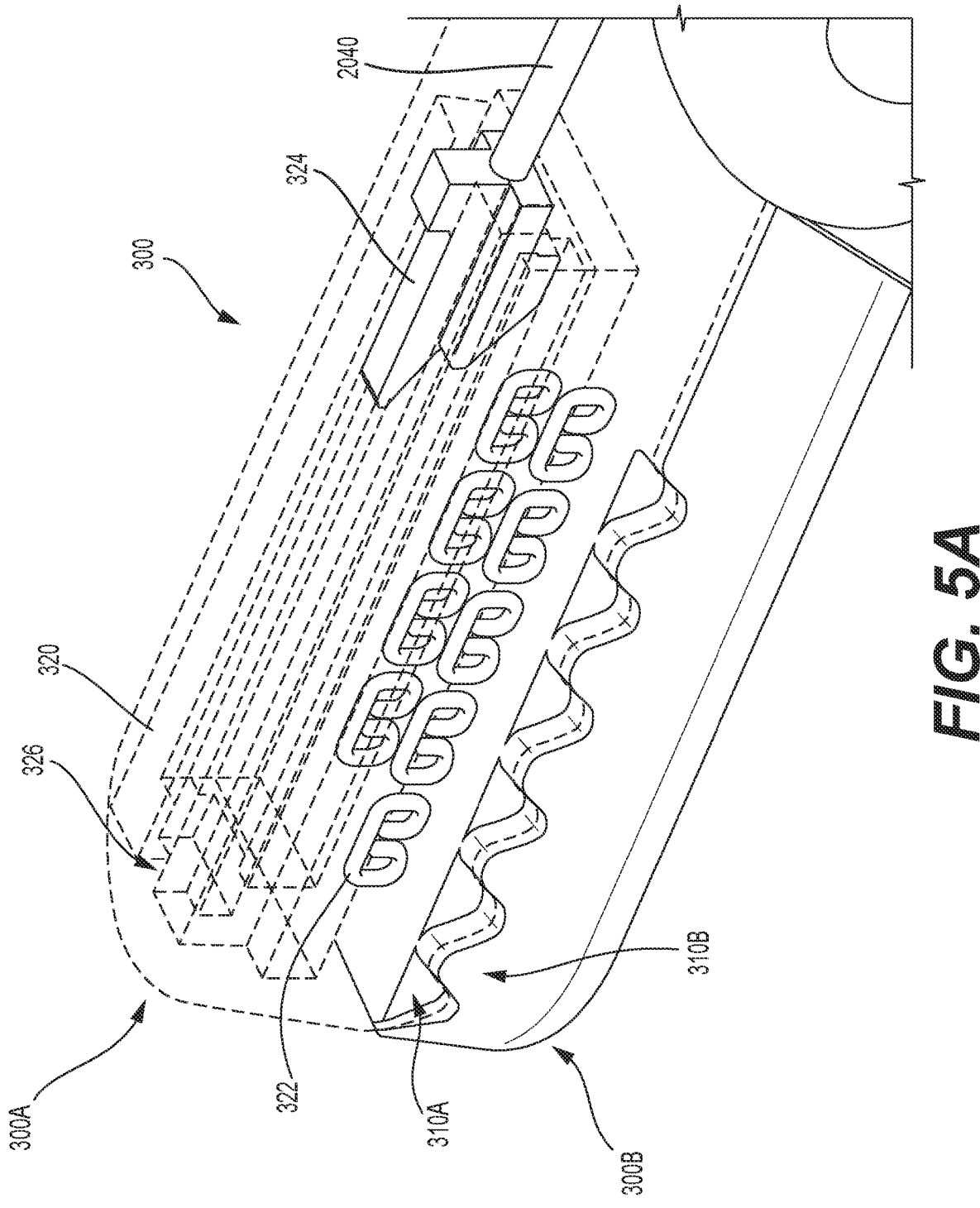
FIG. 5A depicts a partially [transparent] view of the distal portion in the second configuration, according to one or more embodiments.
Figure 5B:
FIG. 5B depicts a partially transparent view of a cartridge and a sled of the distal portion, according to one or more embodiments.

Staple cartridge includes staples 322 (as shown in FIGS. 3A and 3B) and a sled 324. Sled 324 may be slidably received within slot 326 to actuate the staples. Slot 326 is in fluid communication with cavity 340. Sled 324 may have any of the properties of any sled for staple actuation known in the art. For example, as shown in FIG. 5B, sled 324 may have a wedge shape. Sled 324 may be coupled to tube 204 via coupler 2040, or integrally formed with tube 204, such that manipulation of slider 120 (as shown in FIG. 1) moves tube 204 proximally or distally and, therefore, moves sled 324 axially along slot 326. Coupler 2040 may be a linkage that transmits the actuation of tube 204 to the sled 324. As sled 324 moves axially, sled 324 may interact with staples 322, thereby discharging staples 322 out of cartridge 320. Actuation of slider 120 may optionally be disabled in the first, open configuration such that a stapling action is only available when the end effector 300 is in the second, closed, configuration shown in FIG. 3B. In the second configuration, in which upper arm 300A is in contact with lower arm 300B, discharged staples will be discharged toward the one or more recesses 332 on the anvil 330 of lower arm 300B. Recesses 332 may interact with staples 322 to push arms of staples 322 and close staples 322. In the views of FIGS. 5A and 5B, discussed below, staples 322 are shown as if they have been discharged and closed by interacting with recesses 332.

In the second, closed, configuration shown in FIG. 3B, upper teeth 310A mate with lower teeth 310B, and cartridge 320 and anvil 330 may be surrounded on lateral sides by the engaged or mated teeth 310A, 310B. Protrusion 342 may mate with recess 344 distally of cartridge 320 and anvil 330. In operation, a user may actuate trigger 114 to grasp tissue or another object by the mated teeth 310A, 310B (and the mated protrusion 342 and recess 344). Once the tissue or object is grasped, a user may actuate slider 120 to discharge staples from cartridge 320 through the tissue or object onto anvil 330. The recesses 332 on anvil 330 may be configured to form the staples into a desirable shape for proper stapling, such as a B-shape, as shown in FIGS. 5A and 5B, discussed below.

FIG. 5A depicts a partially transparent view of upper arm 300A of the end effector 300 in the second configuration, according to one or more embodiments. In this view, the cartridge 320 is visible, with staples 322 having been discharged and formed into the B-shape. The bottom edges of staples 322 were curved upward by recesses 332 formed in anvil 330. In the second configuration, the surface of anvil 330 may be level with the upper surface of the ridges of lower teeth 310B and the upper surface of the recesses between ridges of upper teeth 310A.

FIG. 5B depicts a transparent view of the cartridge 320, with the sled 324 positioned therein, according to one or more embodiments. In FIG. 5B, sled 324 is at rest at a proximal end of the cartridge 320, with sled 324 having been retracted proximally after staples 322 were delivered. Prior to delivery of staples 322, upon axially moving slider 120 (FIG. 1) distally, the sled 324, which is coupled to tube 204, is pushed toward the distal end of cartridge 320, traveling within slot 326. As discussed below, such distal movement of sled 324 may delivery the staples 322.

Sled 324 includes a central body 324A, a protruding tab 324B, a central sloped portion 324C on a distal end face of central body 324A, and a lateral body 324E that extends from both lateral sides of central body 324A. Lateral body 324E may include a distal end face with lateral sloped portion 324D. Upon motion of the sled 324 in the distal direction within slot 326, the central sloped portion 324C and/or the lateral sloped portion 324D make contact with the staples 322 and force them downward out of cartridge 320 toward anvil 330 in a stapling action. As shown in FIG. 5B, sled 324 may be retracted proximally following delivery. For example, slider 120 may be biased proximally by a spring or other structure, such that sled 324 is retained in a proximal position until a user desires to deliver staples 322, and sled 324 returns to the biased proximal position following staple delivery.

Figure 5C:
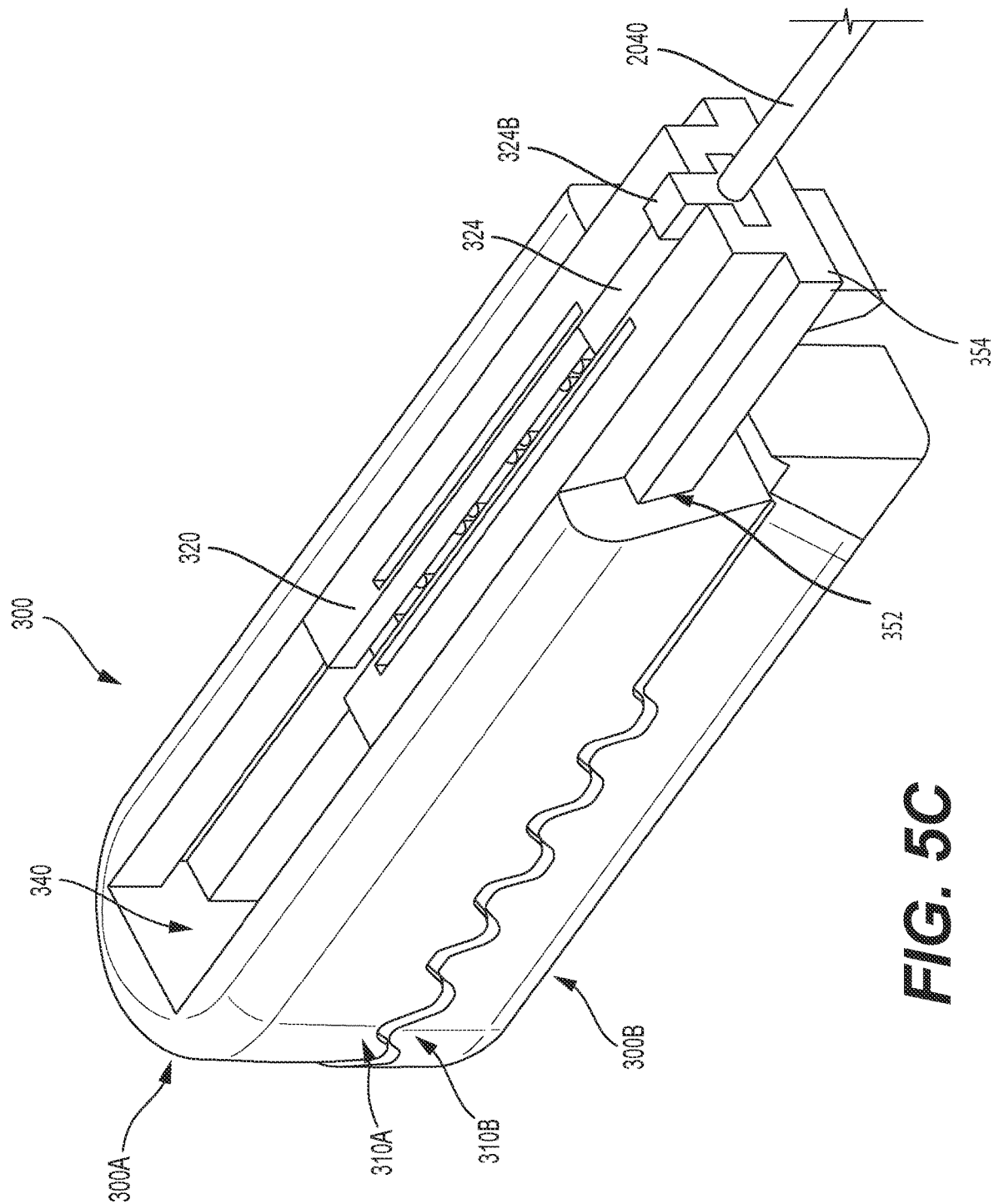
FIG. 5C depicts a perspective view of the distal portion, according to one or more embodiments.

FIG. 5C depicts a loading or unloading of the cartridge 320 into upper arm 300A of end effector 300. The upper arm 300A of end effector 300 includes cavity 340 for receiving cartridge 320. Cavity 340 may have an open proximal end and closed distal and lateral sides. Cartridge 320 (and sled 324) may be inserted into the proximal opening of cavity 340, which may be on a proximal end of upper arm 300A, and advanced toward the distal end of cavity 340. In some examples, sled 324 may be inserted into cartridge 320 before loading cartridge 320 into cavity 340. In other examples, sled 324 may be non-removably coupled to cartridge 320 and may be removably coupled to tube 204 (e.g., via control member 2040). The cavity 340 may include a stepped portion 352, and cartridge 320 may include a corresponding stepped portion 354 for engaging within the stepped portion 352 to secure the cartridge 320 into the end effector 300. For example, stepped portions 352, 354 may extend laterally outwardly from central portions of cavity 340 and cartridge 320, respectively. Protruding tab 324B may aid the user in loading the sled 324 into the cartridge 320 and may aid in retaining cartridge 320 within cavity 340. In some examples, the staples may be preloaded into cartridge 320. The staples 322 may be arranged in two parallel rows in the axial direction, as shown in FIGS. 5A-5C, or may be arranged in other configurations, such as perpendicular to the axial direction and parallel to each other, or in a single row in the axial direction.

Figure 6A:
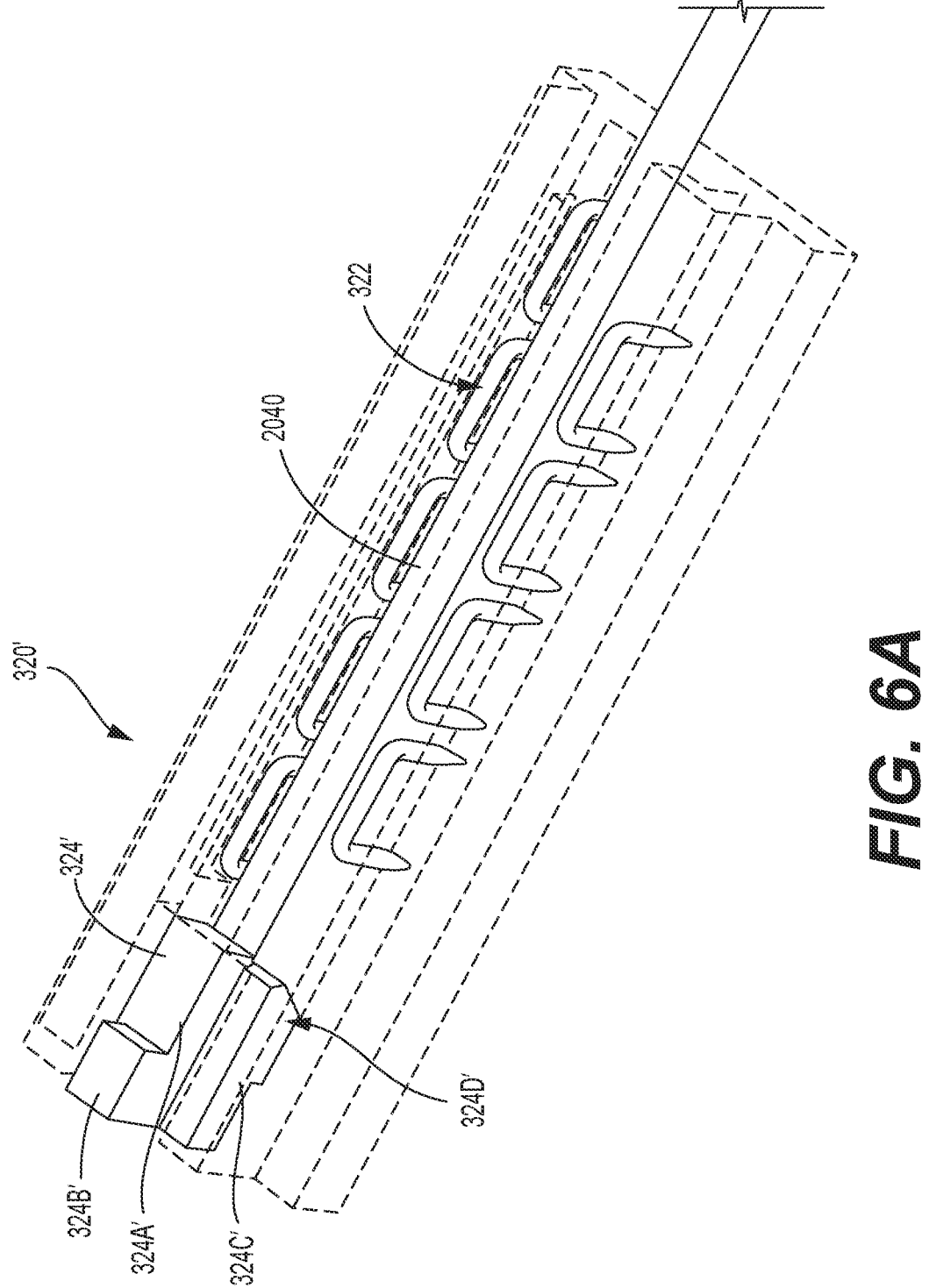
FIG. 6A depicts a partially transparent view of the cartridge and the sled of the distal portion, according to one or more embodiments.
Figure 6B:
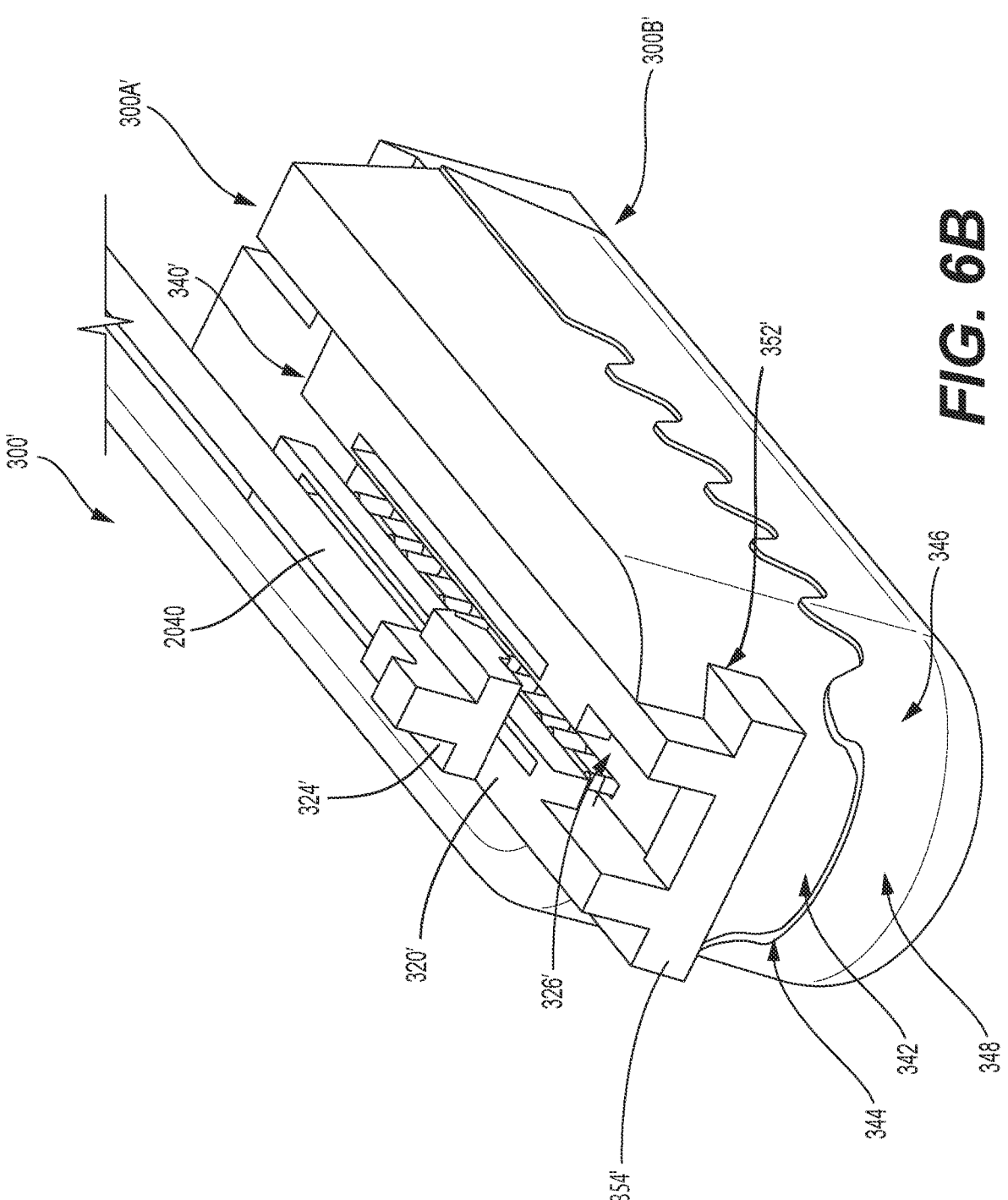
FIG. 6B depicts a perspective view of the distal portion, according to one or more embodiments.

FIG. 6A depicts a transparent view of another exemplary cartridge 320', along with an alternative sled 324'. Sled 324' includes a central body 324A', a protruding tab 324B', a central sloped portion 324C' on a distal end face of central body 324A, and a lateral sloped portion 324D' extending from either side of central sloped portion 324C'. Unless otherwise provided herein, cartridge 320' may have any of the features of cartridge 320. In some embodiments, sled 324' may deliver staples 322 by travelling from a distal end of cartridge 320' toward a proximal end cartridge 320' to perform a stapling function. Thus, sled 324' may actuate staples by moving in a direction opposite to sled 324. In FIG. 6A, the staples 322 are shown in an unactuated, substantially rectangular shape, with sled 324' at a distal end of cartridge 320'. As sled 324' traverses over the staples 322 within slot 326' of cartridge 320', the staples are discharged or deployed via contact from the sloped portions 324C' and 324D'. Slot 326' is in fluid communication with cavity 340'. In such an example, slider 120 (FIG. 1) may be biased distally, rather than proximally, and proximal movement of slider 120 may deliver staples 322.

FIG. 6B depicts an isometric view of an end effector 300' to be used in conjunction with cartridge 320' of FIG. 6A, according to one or more embodiments. Unless otherwise specified herein, end effector 300' may have any of the properties of end effector 300. FIG. 6B demonstrates a loading of the cartridge 320' into an upper arm 300A' of end effector 300'. The upper arm 300A' of end effector 300' may include a cavity 340' for receiving cartridge 320'. Cavity 340' may have an open distal end and closed lateral and/or proximal ends. Cartridge 320' and sled 324' may be inserted into the open distal end of cavity 340' and advanced toward the proximal end of cavity 340'. In some examples, sled 324' may be removably coupled to cartridge 320'. In other alternatives, sled 324' may be non-removably coupled to cartridge 320'. Sled 324' may be integrally with control member 2040 (which may be coupled to tube 204, as discussed above) or may be attached to control member 2040 before loading sled 324' and cartridge 320' into cavity 340' of the upper arm 300A'. Similar to cavity 340 and cartridge 320, the cavity 340' may include a stepped portion 352', and cartridge 320' may include a corresponding stepped portion 354' for engaging within the stepped portion 352' to secure the cartridge 320' into the end effector 300'.

For either one of end effectors 300 and 300', the operation for grasping and stapling includes the same steps. First, a cartridge 320 is loaded into the end effector 300, or an end effector 300 with a preloaded cartridge 320 is supplied. The cartridge 320 may include one or more staples 322. The staples may 322 may be situated in two rows, as shown, or one row, or more than two rows. Next, a target site is accessed using the endoscope, the target site including a tissue defect or other area to be stapled. The trigger 114 is actuated to grasp the target tissue or object, with a squeezing of the trigger 114 closing the upper arm 300A/300A' onto the lower arm 300B, and a releasing of the trigger opening or separating the arms 300A/300A', 300B from one another.

Once the tissue or object is grasped and closed within the arms 300A/300A', 300B, the slider 120 may be moved proximally or distally, as disclosed above, to axially translate the sled 324 or 324' to discharge or deploy the staples 322. The staples 322 may only discharge if the arms 300A/300A', 300B are in a closed position. Once the staples 322 have been deployed, the user may release the slider 120 and/or the trigger 114, releasing the tissue or other target object from arms 300A/300A', 300B.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device comprising:
an end effector having:
an upper arm comprising:
a first plurality of teeth; and
a second plurality of teeth;
a lower arm comprising:
a third plurality of teeth;
a fourth plurality of teeth; and
an anvil, wherein the third plurality of teeth are on a first lateral side of the anvil and the fourth plurality of teeth are on a second lateral side of the anvil, and wherein the second lateral side of the anvil is opposite the first lateral side of the anvil; and
a cartridge positioned in a cavity of the upper arm, such that the first plurality of teeth are on a first lateral side of the cartridge and the second plurality of teeth are on the second lateral side of the cartridge, wherein the second lateral side of the cartridge is opposite the first lateral side of the cartridge;
a cable coupled to the upper arm, wherein the cable is configured to rotate the upper arm;
a tube coupled to a sled received within the cartridge, wherein the sled is configured to deliver staples, and wherein at least a portion of the cable is disposed within the tube;
a shaft coupled to the end effector; and
an operation portion coupled to the shaft.

2. The medical device of claim 1, wherein the cable is coupled to a trigger of the operation portion.

3. The medical device of claim 2, wherein the tube is coupled to a slider of the operation portion.

4. The medical device of claim 1, wherein a distal portion of the upper arm includes a protrusion; and
wherein a distal portion of the lower arm includes a recess configured to mate with the protrusion.

5. The medical device of claim 1, wherein each of the third plurality of teeth and the fourth plurality of teeth of the lower arm includes a plurality of ridges and a plurality of recesses, wherein the plurality of recesses are recessed with respect to a surface of the anvil.

6. The medical device of claim 5, wherein the surface of the anvil is planar.

7. The medical device of claim 6, wherein upper surfaces of the third plurality of teeth and upper surfaces of the fourth plurality of teeth are approximately level with the surface of the anvil.

8. The medical device of claim 6, wherein each of the first plurality of teeth and the second plurality of teeth includes a plurality of ridges and a plurality of recesses, wherein lower surfaces of the plurality of ridges of the first plurality of teeth and lower surfaces of the plurality of ridges of the second plurality of teeth are below the surface of the anvil when the end effector is in a closed configuration.

9. The medical device of claim 8, wherein upper surfaces of the plurality of recesses of the first plurality of teeth and the plurality of recesses of the second plurality of teeth of the upper arm are approximately level with the anvil in the closed configuration.

10. The medical device of claim 1, wherein the third plurality of teeth and the fourth plurality of teeth are arranged approximately linearly, wherein the lower arm further includes a first distal tooth distal of the first plurality of teeth and a second distal tooth distal of the second plurality of teeth, wherein the first distal tooth and the second distal tooth are disposed on a curved surface between a lateral side surface of the lower arm and a distal surface of the lower arm.

11. The medical device of claim 1, wherein the first plurality of teeth and the second plurality of teeth extend downward from a surface of the upper arm that defines the cavity.

12. The medical device of claim 1, wherein the cavity has an open proximal end for slidably receiving the cartridge.

13. The medical device of claim 1, wherein the cavity has an open distal end for slidably receiving the cartridge.

14. The medical device of claim 1, wherein the upper arm has a first stepped portion, and wherein the cartridge has a second stepped portion configured to mate with the first stepped portion.

15. A medical device comprising:
an end effector having:
an upper arm comprising a first plurality of teeth;
a lower arm comprising a second plurality of teeth and an anvil; and
a cartridge positioned in a cavity of the upper arm;
a shaft coupled to the end effector, the shaft including:
a cable coupled to the upper arm, the cable configured to rotate the upper arm; and
a tube coupled to a sled received within the cartridge, the sled configured to deliver staples, wherein at least a portion of the cable is disposed within the tube; and
an operation portion coupled to the shaft.

16. The medical device of claim 15, wherein the cavity has an open proximal end for slidably receiving the cartridge, or wherein the cavity has an open distal end for slidably receiving the cartridge.

17. A medical device comprising:
an end effector having:
an upper arm comprising a first plurality of teeth;
a lower arm comprising a second plurality of teeth and an anvil, wherein the second plurality of teeth includes a plurality of ridges and a plurality of recesses, and wherein the plurality of recesses are recessed with respect to a surface of the anvil;
a cartridge positioned in a cavity of the upper arm;
a shaft coupled to the end effector; and
an operation portion coupled to the shaft.

18. The medical device of claim 17, wherein the surface of the anvil is planar, and wherein upper surfaces of the second plurality of teeth are approximately level with the surface of the anvil.

19. The medical device of claim 18, wherein the first plurality of teeth includes: a plurality of ridges and a plurality of recesses, wherein lower surfaces of the plurality of ridges of the first plurality of teeth are below the surface of the anvil when the end effector is in a closed configuration.

20. The medical device of claim 17, further comprising:
a cable coupled to the upper arm, the cable configured to rotate the upper arm; and
a tube coupled to a sled received within the cartridge, the sled configured to deliver staples, wherein at least a portion of the cable is disposed within the tube.

* * * * *